(12) United States Patent
Urano et al.

(10) Patent No.: US 7,965,386 B2
(45) Date of Patent: Jun. 21, 2011

(54) METHOD AND ITS APPARATUS FOR INSPECTING DEFECTS

(75) Inventors: Yuta Urano, Yokohama (JP); Toshiyuki Nakao, Yokohama (JP); Yoshimasa Oshima, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 12/964,249

(22) Filed: Dec. 9, 2010

(65) Prior Publication Data

US 2011/0080578 A1  Apr. 7, 2011

Related U.S. Application Data

(63) Continuation of application No. 12/414,727, filed on Mar. 31, 2009, now Pat. No. 7,869,024.

(30) Foreign Application Priority Data

Mar. 31, 2008  (JP) .................. 2008-089870

(51) Int. Cl.
*G01N 21/00* (2006.01)
(52) U.S. Cl. .................................................. 356/237.2
(58) Field of Classification Search ............... 356/237.2, 356/364, 369; 250/559.04–559.09
See application file for complete search history.

(56) References Cited

U.S. PATENT DOCUMENTS

| 6,894,302 B2 | 5/2005 | Ishimaru et al. |
| 7,242,016 B2 | 7/2007 | Ishimaru et al. |
| 7,417,244 B2 * | 8/2008 | Ishimaru et al. ......... 250/559.46 |
| 2009/0187354 A1 * | 7/2009 | Ooyama et al. ................ 702/40 |

FOREIGN PATENT DOCUMENTS

| JP | 09-304289 | 11/1997 |
| JP | 2001-255278 | 9/2001 |
| JP | 2003-240730 | 8/2003 |
| JP | 2008-032621 | 2/2008 |

* cited by examiner

*Primary Examiner* — Roy Punnoose
(74) *Attorney, Agent, or Firm* — Antonelli, Terry, Stout & Kraus, LLP.

(57) ABSTRACT

A defect inspection apparatus is capable of inspecting an extremely small defect present on the top and edge surfaces of a sample such as a semiconductor substrate or a thin film substrate with high sensitivity and at high speed. The defect inspection apparatus has an illumination optical system, a plurality of detection optical units and a signal processor. One or more of the detection optical units receives either light diffracted from an edge portion of the sample or light diffracted from an edge grip holding the sample. The one or more of the detection optical units shields the diffracted light received by the detection optical unit based on a signal obtained by monitoring an intensity of the diffracted light received by the detection optical unit in order to inspect a sample portion located near the edge portion and a sample portion located near the edge grip.

7 Claims, 12 Drawing Sheets

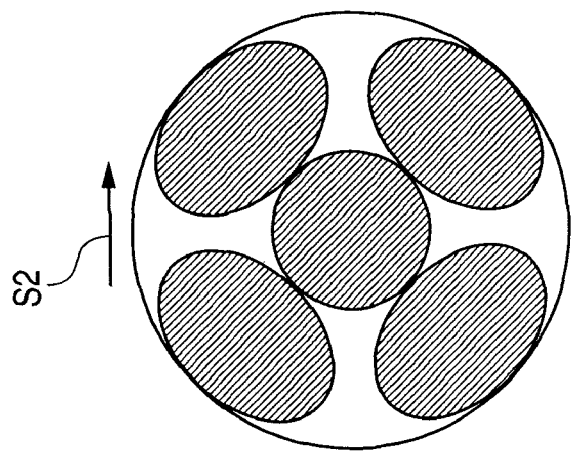
FIG. 4B2
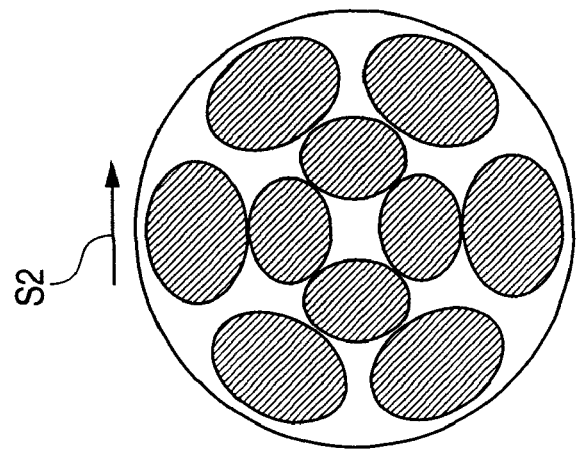
FIG. 4B1
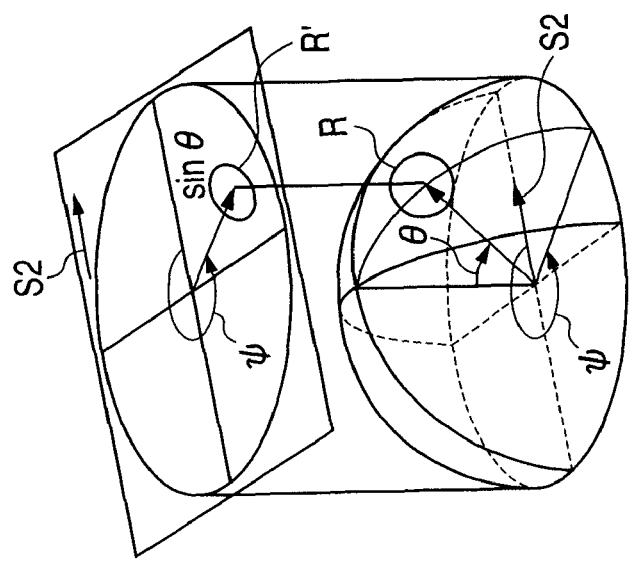
FIG. 4A

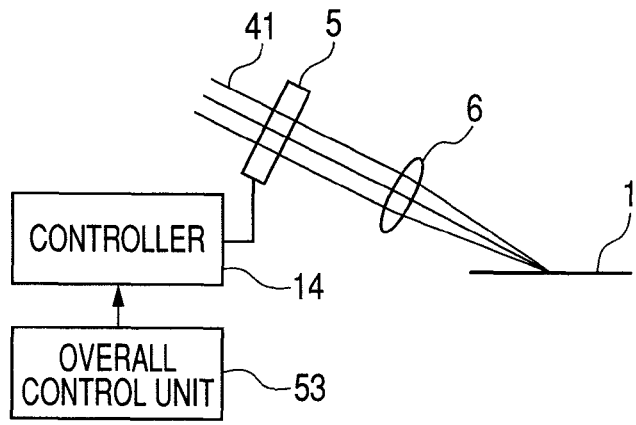
FIG. 5A
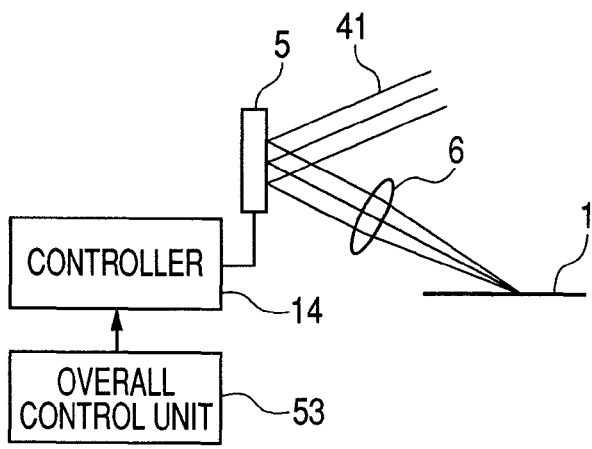
FIG. 5B
FIG. 5C 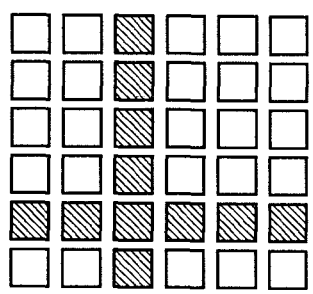   FIG. 5D 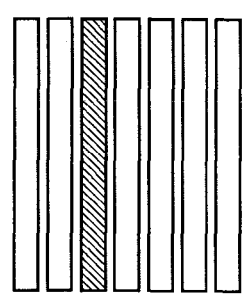
FIG. 5E
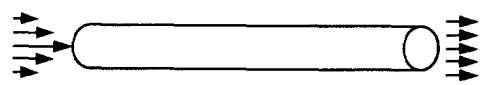

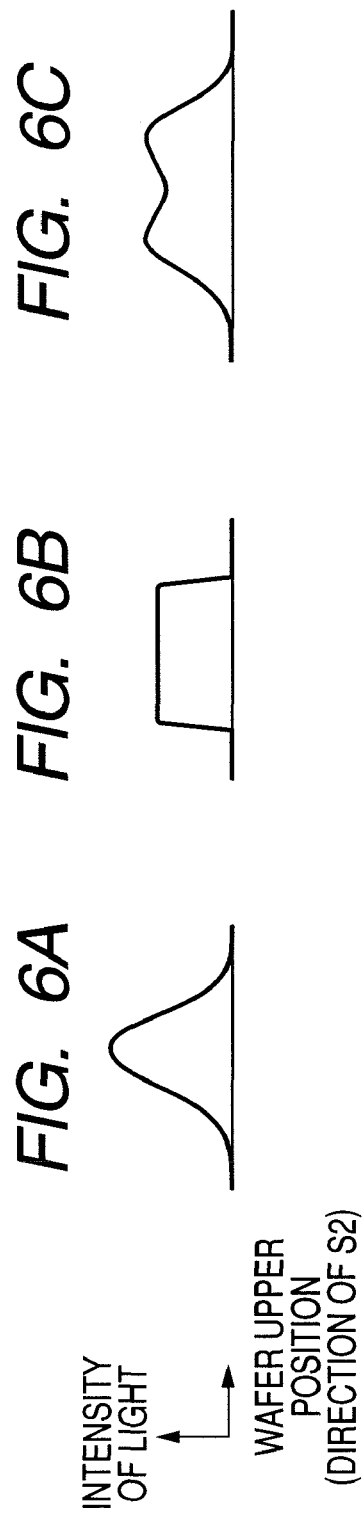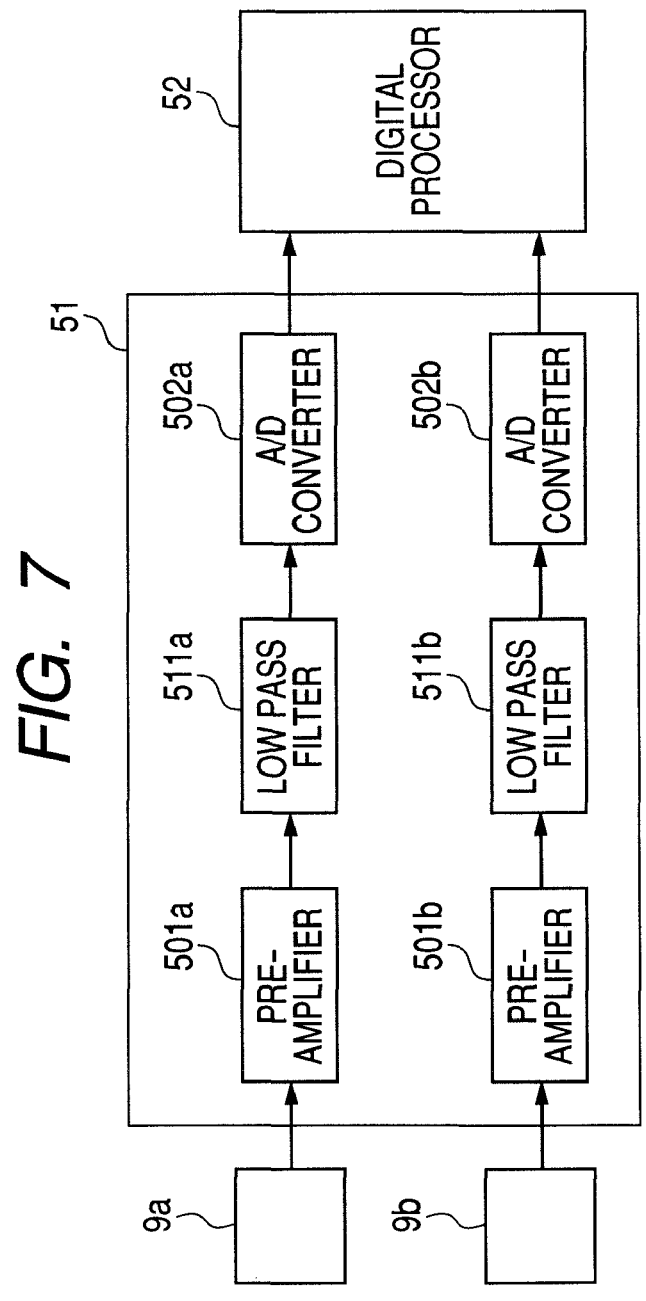

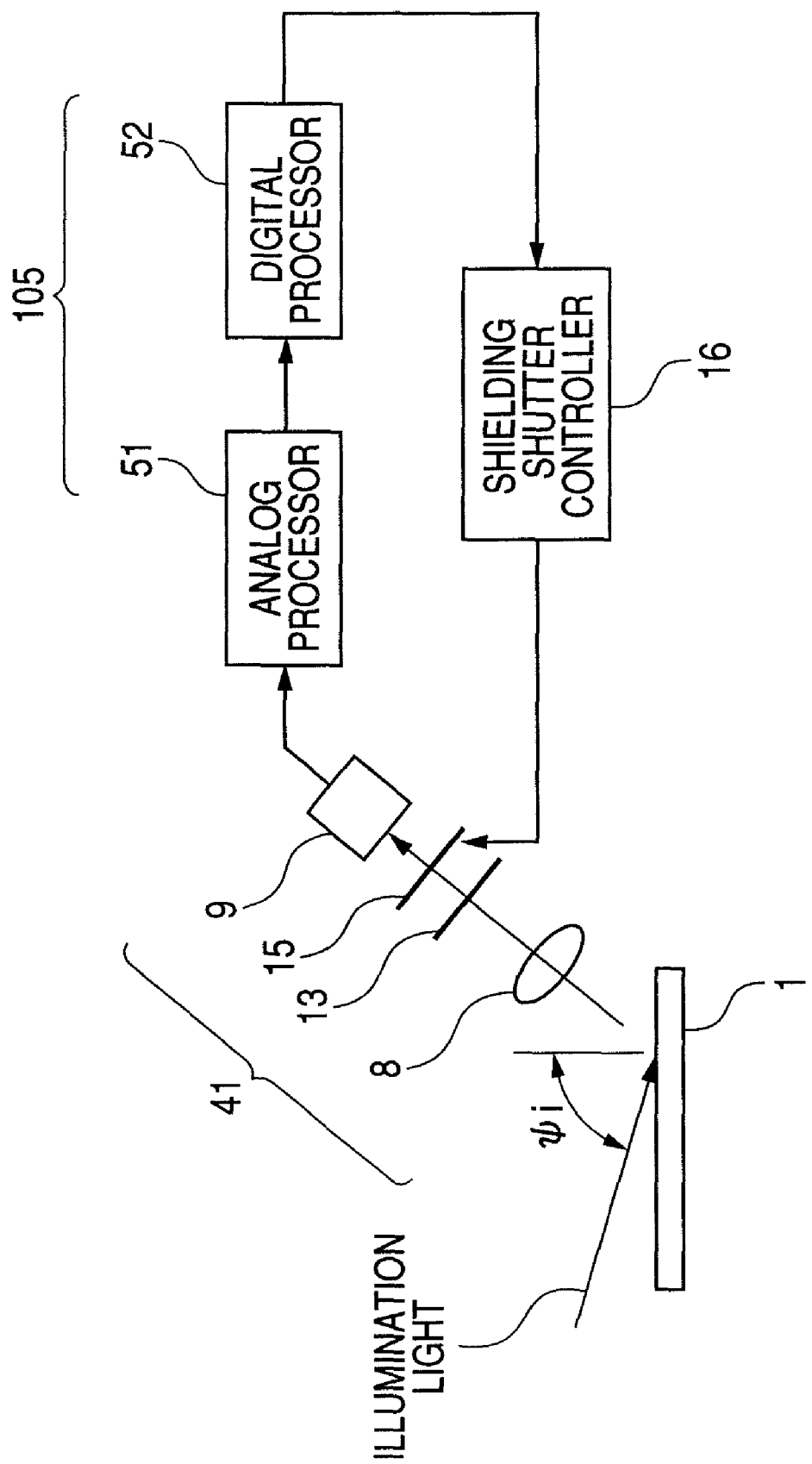

METHOD AND ITS APPARATUS FOR INSPECTING DEFECTS

CROSS REFERENCE TO RELATED APPLICATION

This application is a continuation of U.S. application Ser. No. 12/414,727, filed Mar. 31, 2009, now U.S. Pat. No. 7,869,024 the contents of which are incorporated herein by reference.

BACKGROUND OF THE INVENTION

The present invention relates to a method and apparatus for inspecting a defect present on the top and edge surfaces of a sample such as a semiconductor substrate and a thin film substrate with high sensitivity and at high speed.

In a production line for a semiconductor substrate or for a thin film substrate, an inspection operation is performed to inspect a defect on the surface of the semiconductor substrate or on the surface of the thin film substrate in order to maintain or improve the yield of products.

As a conventional method and apparatus for inspecting a defect, JP-A-H09-304289 (Patent Document 1), JP-A-2003-240730 (Patent Document 2) and JP-A-2008-32621 (Patent Document 3) are known.

Patent Document 1 discloses an apparatus for inspecting the surface of a wafer. The apparatus described in Patent Document 1 has a low-angle optical receiver and a high-angle optical receiver. The low-angle optical receiver is located such that it forms an elevation angle of 30 degrees or less with respect to the surface of the wafer, while the high-angle optical receiver is located such that it forms an elevation angle of more than 30 degrees with respect to the surface of the wafer. The apparatus uses a laser beam to scan the wafer. Each of the low-angle and high angle optical receivers receives light scattered from the wafer illuminated with the laser beam to detect a foreign material by means of the scanning. The foreign material detected from a certain area of the wafer by only the high-angle optical receiver is treated as a crystal defect, while the foreign material detected from the certain area of the wafer by the low-angle optical receiver is treated as an attached foreign material.

Patent Document 2 discloses an apparatus for inspecting the surface of a wafer. The apparatus described in Patent Document 2 has a detector. Light scattered from an edge portion of the wafer has high directivity and is distributed in a direction extending from the edge portion and parallel to a normal to the surface of the wafer. Light scattered from a defect (such as a foreign material) present on the edge portion of the wafer does not exhibit high directivity. A detector(s) detects the light scattered from the defect under the condition that one or more detection optical units are arranged in a direction(s) other than the direction extending from the edge portion and parallel to the normal to the surface of the wafer and do not receive the light scattered from the edge portion. Alternatively, the detector(s) detects the light scattered from the defect, while a space filter(s) arranged on a Fourier transform surface(s) of the one or more detection optical units shields the light scattered from the edge portion.

Patent Document 3 discloses an apparatus for inspecting the surface of an object that is to be inspected. The apparatus described in Patent Document 3 irradiates and scans the surface of the object with a light beam to detect light scattered from the object. The apparatus has a position detection unit for detecting the relative position of the object to the position of a spot of the light beam. The apparatus also includes one of the following: a light shielding unit for preventing the scattered light from being incident on a detector for detecting the scattered light before the spot of the light beam detected by the position detection unit reaches an edge portion of the object; an optical path shielding mechanism for shielding the light beam on an optical path of the light beam before the spot of the light beam detected by the position detection unit reaches the edge portion of the object; and a controller for stopping a function of the detector for detecting the scattered light before the spot of the light beam detected by the position detection unit reaches the edge portion of the object. The apparatus reduces degradation of the detector due to the scattered light. In addition, Patent Document 3 describes that when the light beam reaches the edge portion of the object, the apparatus scans the object with the light beam to prevent an increase in the amount of the light scattered toward the detector from the edge portion.

In a process for manufacturing a semiconductor substrate or the like, a portion of the substrate, which is located near an outer circumferential edge portion (hereinafter referred to as an edge portion) of the substrate, may easily have a defect such as peeling. It is, therefore, necessary to inspect the defect present on the edge portion of the substrate and deal with the defect present on the edge portion early or in advance. A challenge is to maximize the total area of a chip(s) that is included in the total area of the substrate and can be used as a good product(s) and thereby to improve the yield of the product(s).

However, the defect inspection on the edge portion is not taken into account in Patent Document 1.

The apparatus described in Patent Document 2 may have a detection optical unit that does not receive light having high directivity and diffracted from the edge portion. Alternatively, the apparatus described in Patent Document 2 may be configured with the space filter that shields the light diffracted from the edge portion and having high directivity to prevent the detector from detecting the diffracted light. The apparatus described in Patent Document 3 prevents the scattered light (diffracted light) from being incident on the detector for detecting the scattered light, or shields the light beam on the optical path, or stops the function of the detector for detecting the scattered light, before the spot of the light beam detected by the position detection unit reaches the edge portion of the object. This prevents the light scattered (diffracted) from the edge portion from being detected.

However, Patent Documents 2 and 3 do not sufficiently take into account the inspection of a substrate portion located near the edge portion of the substrate at high speed and with high sensitivity.

SUMMARY OF THE INVENTION

The present invention provides a method and apparatus for inspecting a minute defect present on the top and edge surfaces of a substrate such as a semiconductor substrate and a thin film substrate with high sensitivity and at high speed.

According to the present invention, an apparatus for inspecting a defect includes: an illumination optical system for guiding light emitted by a light source onto a sample to illuminate a particular area of the sample as an illumination area;

a plurality of detection optical units for converging from a plurality of directions light generated from the sample when illuminated by the illumination optical system to obtain detection signals of the light on a direction-by-direction basis; and a signal processor for processing a plurality of detection signals obtained by the plurality of detection optical units to judge whether or not a defect is present on the sample;

wherein upon inspection of a near-edge portion of the sample, in a detection optical unit, of the plurality of detection optical units, on which diffracted light generated from the near edge portion is incident, the incident diffracted light is blocked (shielded) by diffracted light blocking means (diffracted light shielding means) in accordance with a signal obtained by monitoring the intensity of the incident diffracted light.

According to the present invention, an apparatus for inspecting a defect includes: an illumination optical system for guiding light emitted by a light source onto a sample to illuminate a particular area of the sample as an illumination area;

a plurality of detection optical units for converging from a plurality of directions light generated from the sample when illuminated by the illumination optical system to obtain detection signals of the light on a direction-by-direction basis; and a signal processor for processing a plurality of detection signals obtained by the plurality of detection optical units to judge whether or not a defect is present on the sample;

wherein upon inspection of a near edge grip portion of the sample, in a detection optical unit, of the plurality of detection optical units, on which diffracted light generated from an edge grip portion is incident, the incident diffracted light is blocked (shielded) by diffracted light blocking means (diffracted light shielding means) in accordance with a signal obtained by monitoring the intensity of the incident diffracted light.

According to the present invention, an apparatus for inspecting a defect includes: an illumination optical system for guiding light emitted by a light source onto a sample to illuminate a particular area of the sample as an illumination area;

a plurality of detection optical units for converging from a plurality of directions light generated from the sample when illuminated by the illumination optical system to obtain detection signals of the light on a direction-by-direction basis; and a signal processor for processing a plurality of detection signals obtained by the plurality of detection optical units to judge whether or not a defect is present on the sample;

wherein upon inspection of a near edge portion and a near edge grip portion of the sample, in a detection optical unit, of the plurality of detection optical units, on which is incident either diffracted light generated from the near edge portion or diffracted light generated from an edge grip portion, the diffracted light incident on the detection optical unit is blocked by diffracted light blocking means in accordance with a signal obtained by monitoring the intensity of the incident diffracted light.

According to the present invention, an apparatus for inspecting a defect includes: an illumination optical system for guiding light emitted by a light source onto a sample to illuminate a particular area of the sample with polarized light;

a plurality of detection optical units for converging from a plurality of directions light generated from the sample when illuminated with the polarized light by the illumination optical system to obtain detection signals of the light on a direction-by-direction basis; and a signal processor for processing a plurality of detection signals obtained by the plurality of detection optical units to judge whether or not a defect is present on the sample;

wherein upon inspection of a near edge portion and a near edge grip portion of the sample, in a detection optical unit, of the plurality of detection optical units, on which is incident either diffracted light generated from the near edge portion or diffracted light generated from an edge grip portion, the polarization components of the diffracted light incident on the detection optical unit are blocked by a polarizing filter.

According to the present invention, the edge grip holding the sample has roughness (on the top and edge surfaces thereof) small enough to ensure that light scattered from the edge grip has a smaller intensity than that of light scattered from a defect present on the sample or that the light detectors are not saturated by light. In addition, the edge grip has a three-dimensional shape to prevent light diffracted from the edge grip from being incident on a main light detector.

According to the present invention, a portion of the sample, which is located near the edge portion of the sample, can be inspected with high sensitivity in a similar manner to inspection of a top surface of the sample.

These and other objects, features and advantages of the invention will be apparent from the following more particular description of a preferred embodiment of the invention, as illustrated in the accompanying drawings.

BRIEF DESCRIPTION OF THE DRAWINGS

FIG. 4A is a diagram showing an angular range in which detection optical units detect scattered light.

FIG. 4B1 is a schematic diagram showing the case where four low-angle detection optical units and four high-angle detection optical units are arranged.

FIG. 4B2 is a diagram showing the case where four low-angle detection optical units and one high-angle detection optical unit are arranged.

FIG. 5A is a diagram showing the configuration of part of an illumination optical system in the case where a transparent optical element is used as an illumination intensity distribution control element.

FIG. 5B is a diagram showing the configuration of part of the illumination optical system in the case where a reflective optical element is used as the illumination intensity distribution control element.

FIG. 5C is a plan view of the illumination intensity distribution control element having a function for two-dimensionally changing the intensity or phase of light passing through the optical element in a surface of the optical element that is perpendicular to an optical axis of the optical element.

FIG. 5D is a plan view of the illumination intensity distribution control element having a function for one-dimensionally changing the intensity or phase of light passing through the optical element in the surface of the optical element that is perpendicular to the optical axis of the optical element.

FIG. 5E is a perspective view of the illumination intensity distribution control element having an inner surface coated by reflective coating and exhibiting a fixed transmittance distribution or a fixed phase distribution.

FIG. 6A is a graph showing an illumination intensity distribution of a laser beam emitted by a laser source, the illumination intensity distribution being represented by substantial Gaussian distribution.

FIG. 6B is a graph showing a uniform illumination intensity distribution of a laser beam emitted by the laser source.

FIG. 6C is a graph showing an illumination intensity distribution of a laser beam emitted by the laser source, the illumination intensity distribution dropped an intensity of a central portion compared with the uniform illumination intensity distribution shown in FIG. 6B.

FIG. 7 is a block diagram showing an analog processor included in a signal processor.

FIG. 11 is a diagram showing the configuration of a light shielding unit that is adapted to shield the light diffracted from the edge portion and included in a detection optical unit that receives the light diffracted from the edge portion.

DESCRIPTION OF THE PREFERRED EMBODIMENTS

Figure 1:
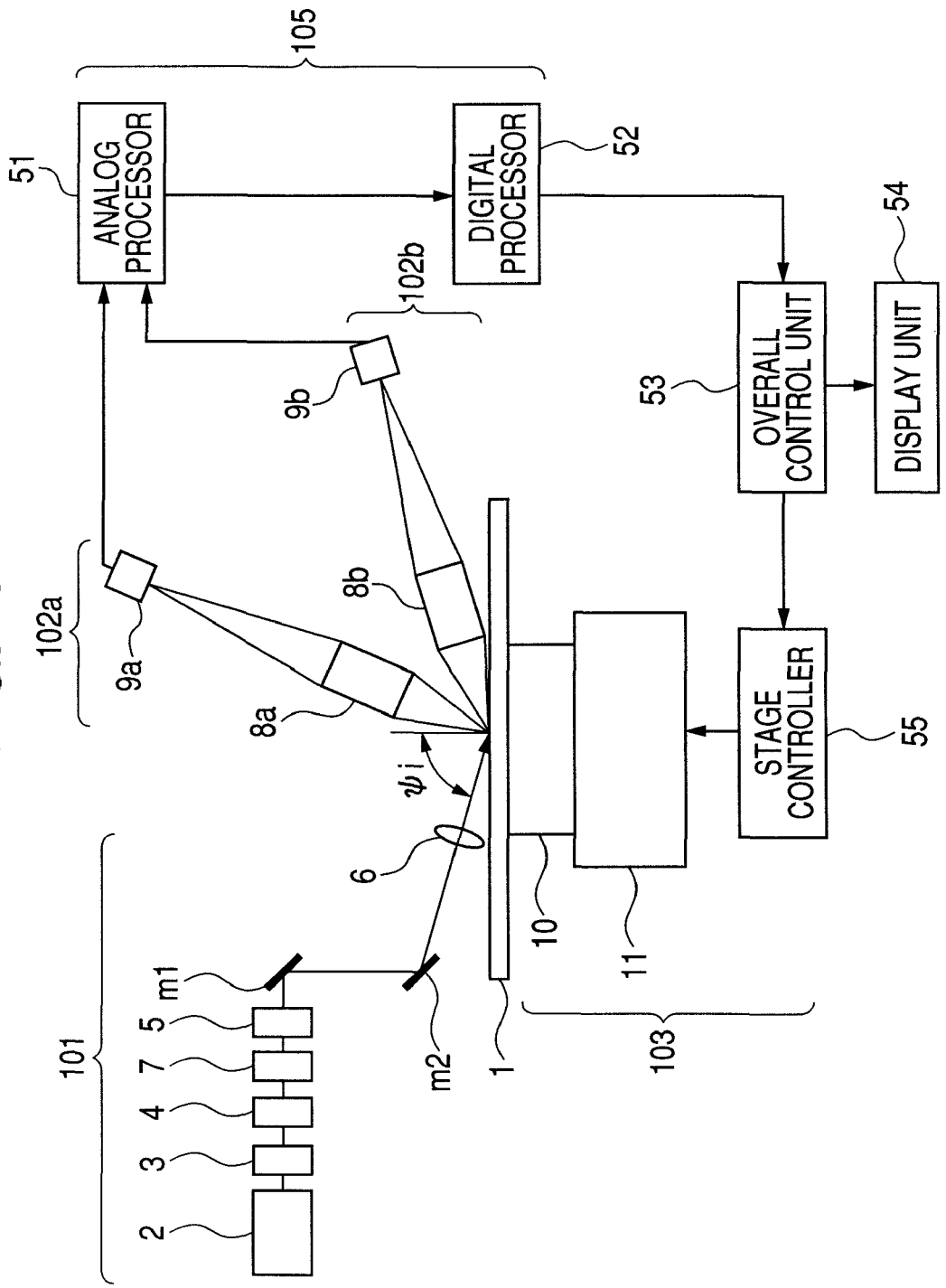
FIG. 1 is a diagram showing the outline configuration of a defect inspection apparatus according to an embodiment of the present invention.

FIG. 1 illustrates the configuration of a defect inspection apparatus according to an embodiment of the present invention. The defect inspection apparatus includes an illumination optical system 101; detection optical units 102a and 102b; a stage 103 capable of mounting a wafer 1 thereon; a signal processor 105; an overall control unit 53; and a display unit 54.

The illumination optical system 101 includes a laser source 2, an attenuator 3, a polarizing element 4, a beam expander 7, an illumination intensity distribution control element 5, reflective mirrors m1 and m2, and a focusing lens 6. The laser source 2 emits a laser beam. The attenuator 3 adjusts the emitted laser beam to a given intensity. The polarizing element 4 then adjusts the intensity-adjusted laser beam to a polarized state desired. The beam expander 7 adjusts the resultant laser beam to a given beam diameter. The diameter-adjusted laser beam is then directed by the reflective mirrors and the focusing lens 6 onto a spot on the wafer 1 to be inspected. The illumination intensity distribution control element 5 is used to control the distribution of illumination intensity across the wafer 1. As shown in FIG. 1, the illumination optical system 101 is configured to illuminate the wafer 1 with a laser beam at an oblique incident angle, meaning that the incident laser beam is oblique to a normal to the surface of the wafer 1. However, the illumination optical system 101 is also capable of illuminating the wafer 1 with a laser beam at the perpendicular incident angle by way of another optical path not shown in FIG. 1. The incident angle of a laser beam can thus be changed according to wafer areas to be inspected.

Used as the laser source 2 upon detection of micro-scale defects present in upper layers of the wafer 1 including its uppermost layer is one that oscillates a short-wavelength ultraviolet or vacuum ultraviolet laser beam and is powerful enough to output such a laser beam of 1 watt or higher. To detect defects located further down from the upper layers, one that oscillates a visible or infrared laser beam is used as the laser beam 2.

Figure 2A:
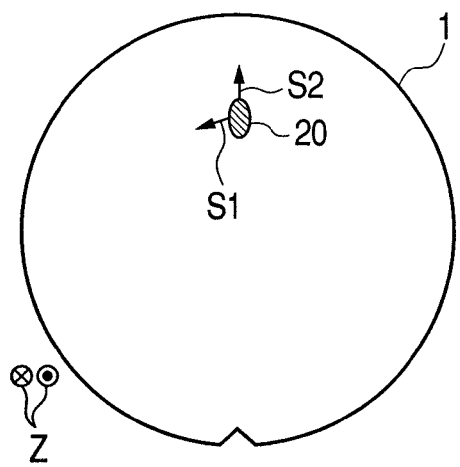
FIG. 2A is a plan view of a wafer and shows the shape of an elliptical illumination area having a long length in a certain direction and a short length in a direction perpendicular to the certain direction.
Figure 2B:
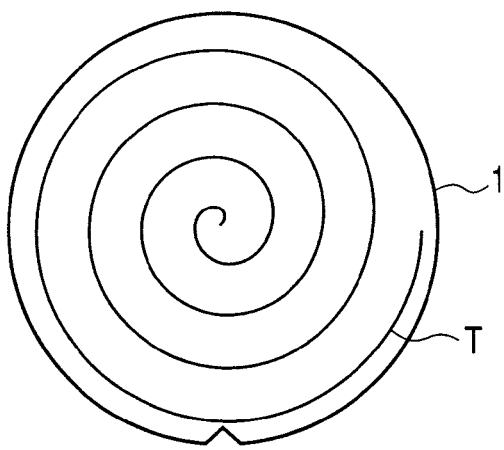
FIG. 2B is a diagram showing a spiral trajectory of the illumination area on the wafer by a rotational movement of a rotary stage and a translational movement of a stage.

The stage 103 has a stage controller 55, a translation stage 11, a rotary stage 10, and a Z stage (not shown). FIG. 2 show the relationship between an illumination area 20 on the wafer 1 and a beam scanning direction (illumination-area moving direction) defined by a rotational movement of the rotary stage 10 and by a translational movement of the translation stage 11 and the resultant trace T of the illumination area across the wafer 1. As shown in FIG. 2A, the illumination area 20 is elliptical in shape, being long in one direction and short in the direction perpendicular to that direction. This shape is formed by illumination intensity distribution control or by oblique illumination by means of the illumination optical system 101. The rotational movement of the rotary stage 10 moves the illumination area 20 in a circumferential direction S1 of a circle that has as its center the rotational axis of the rotary stage 10. In addition, the translational movement of the translation stage 11 moves the illumination area 20 in a translational direction S2 of the translation stage 11. The illumination optical system 101 is configured such that the longitudinal direction of the illumination area 20 is parallel to the direction S2 and such that the illumination area 20 passes through the rotational axis of the rotary stage 10 by beam scanning in the direction S2. The Z stage moves in a height direction of the wafer 1, that is, in an extending direction of a normal to the surface of the wafer 1. The translation stage 11 is designed to move in the direction S2 by a distance equal to or smaller than the longitudinal-direction length of the illumination area 20 during a 360-degree rotation of the rotary stage 10. Such movements of the two stages during beam scanning result in the spiral trace T of the illumination area 20, whereby the laser beam is scanned across the entire surface of the wafer 1.

Figure 3:
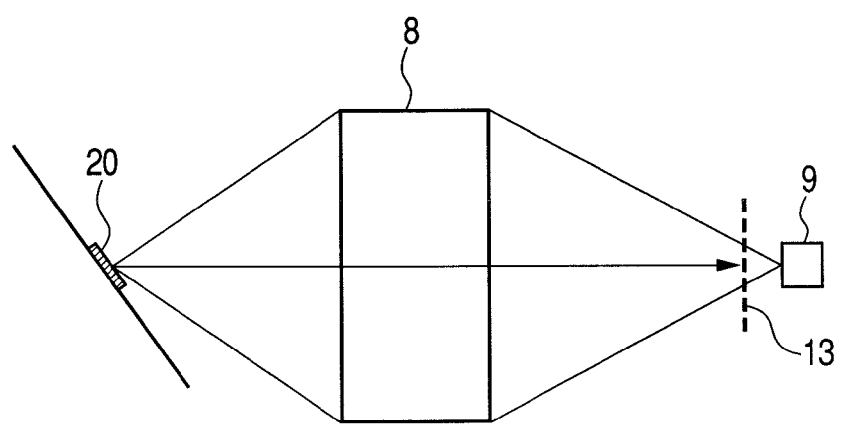
FIG. 3 is a diagram showing the outline configuration of each detection optical unit.

The detection optical unit 102a and 102b are each configured to converge and detect scattered or diffracted lights, but the lights detected differ in direction and angle between those detected by the detection optical unit 102a and those detected by the detection optical unit 102b. FIG. 3 shows the configuration of the detection optical unit 102a. Because the detection optical unit 102b is structurally the same as the detection optical unit 102a, it is not discussed herein. As described later with reference to FIGS. 4B1 and 4B2, the defect inspection apparatus according to the present embodiment includes other detection optical units (not shown in FIG. 1) which are mutually different in addition to the detection optical unit 102a and 102b for the purpose of detecting scattering lights having a wide scatter angular range.

The detection optical unit 102a includes an imaging lens 8, a polarizing filter 13, and a light detector 9. The polarizing filter 13 can be moved into or out of the optical axis A of the imaging lens 8 and can be rotated to change the direction of light detection. The polarizing filter 13 is used to reduce scattered-light components due to wafer roughness and diffracted- or scattered-light components due to the edge of the wafer, both attributable to noise.

The illumination area 20 is focused onto the light detector 9 by the imaging lens 8. To achieve detection of low-intensity lights scattered from foreign particles on the wafer 1, a photomultiplier, an avalanche photodiode, a semiconductor photo-detector having an image intensifier, or the like is used as the light detector 9.

FIGS. 4A to 4B2 are to explain the angular ranges of scattered lights detected by multiple photodetectors according to the invention, or the plural detection optical units 102a and 102b. FIG. 4A is a diagram showing an angular range in which each of the detection optical units detects the scattered light. A hemisphere shown in FIG. 4A has an apex and an equatorial plane. The equatorial plane corresponds to the top surface of the wafer 1. The apex is located in a direction that extends from the center of the top surface of the wafer 1 and is parallel to the normal to the top surface of the wafer 1. An azimuth (longitude) of an optical axis of each of the detection optical units 102 is indicated by φ. The scanning direction S2 (direction of the translational movement of the translation stage 11) is used as a standard to define the azimuth φ. An angle formed between a line connecting the center of the equatorial plane with the apex and a line connecting the center of the equatorial plane with the center of an area R is indicated by θ. The area R indicates the angular range in which each of the detection optical units 102 detects the scattered light. The area R is located on the hemisphere. FIGS. 4B1 and 4B2 are diagrams each showing the equatorial plane when viewed from the apex of the hemisphere. In other words, each of FIGS. 4B1 and 4B2 shows the equatorial plane drawn by parallel-projecting the hemisphere. In FIGS. 4B1 and 4B2, the angular ranges in which the detection optical units 102 detect the scattered light are indicated by hatching. The plurality of detection optical units 102 is provided to cover a wide angular range and thereby capable of detecting a wide variety of defects. An angle at which light is scattered from a defect varies depending on the type and size of the defect. The detection optical units 102 detect intensities of light scattered at different angles. Signals indicating the detected intensities of the light are processed by the signal processor 105 (described later). Thus, the defect inspection apparatus is capable of classifying the types of various defects and estimating the sizes of the defects with high accuracy.

FIG. 4B1 shows an example in which the defect inspection apparatus includes detection optical units 102 suitable to inspect a foreign material of several ten nanometers to several hundred nanometers. Light scattered from an extremely small foreign material and directed at a low angle (with respect to the equatorial plane) has a high intensity in the case where P-polarized light is used for the illumination. Some of the detection optical units 102 can detect an extremely small defect by detecting, from almost all directions, light components scattered at low angles (with respect to the equatorial plane). The other detection optical units 102 can detect a defect (dent) such as a crystal originated particle (COP) (from which light having a high intensity is scattered at a high angle) by detecting light components scattered at a high elevation angle with respect to the equatorial plane. FIG. 4B2 shows an example in which the defect inspection apparatus includes detection optical units 102 having large numerical apertures. In the case where the detection optical units 102 has the large numerical apertures, the detection optical units 102 can detect scattered light having a low intensity and are therefore suitable to detect an extremely small defect.

In both cases, the plurality of detection optical units 102 can detect light scattered in a wide angular range. The detection optical units 102 can detect light scattered from a defect in a direction that varies depending on the type of the defect. Therefore, the detection optical units 102 can robustly detect a wide variety of defects. In addition, the detection optical units 102 detect light components scattered at elevation angles (low and high elevation angles) with respect to the equatorial plane. Thus, the detection optical units 102 can detect a convex defect (such as a foreign material) and a concave defect (such as a COP and a scratch) and classify the defects.

Next, a description is made of the configuration of the illumination intensity distribution control element 5 included in the illumination optical system 101 and a method for controlling an illumination intensity distribution with reference to FIGS. 5A to 6C. FIG. 5A is a diagram showing the configuration of a part of the illumination optical system 101 in the case where a transparent optical element is used as the illumination intensity distribution control element 5. The laser source 2 emits a laser beam 41. The laser beam 41 is adjusted by the illumination optical system 101 to ensure that the laser beam 41 has a desired intensity, desired polarization, and a desired beam diameter. The adjusted laser beam 41 then passes through the illumination intensity distribution control element 5 and is introduced onto the top surface of the wafer 1 via the focusing lens 6. The overall control unit 53 is connected with a controller 14 (shown in FIG. 5A). The overall control unit 53 transmits a signal to the controller 14. The controller 14 receives the signal from the overall control unit 53 and controls the illumination intensity distribution control element 5 based on the received signal. FIG. 5B is a diagram showing the configuration of a part of the illumination optical system 101 in the case where a reflective optical element is used as the illumination intensity distribution control element 5. In addition, the optical element used as the illumination intensity distribution control element 5 has a function for changing the intensity or phase of light that is to pass through the optical element for each two-dimensional area (shown in FIG. 5C) or for each one-dimensional area (shown in FIG. 5D). The function of the optical element changes the intensity or phase of the light on a surface of the optical element that is perpendicular to an optical axis of the optical element. An image formed on a light transmission surface or of the illumination intensity distribution control element 5 is projected on the wafer 1 by the focusing lens 6. That is, the image projected on the wafer 1 is similar to a distribution of intensities of light modulated by the illumination intensity distribution control element 5. A distance between the focusing lens 6 and a point at which the light is incident on the top surface of the wafer 1 and a distance between the focusing lens 6 and the light transmission surface of the illumination intensity distribution control element 5 are set to be the same as a focal length of the focusing lens 6. Thus, a Fourier transform image of a light amplitude distribution, which is formed on the light transmission surface of the illumination intensity distribution control element 5, is projected on the wafer 1. Therefore, the illumination intensity distribution provided by the illumination intensity distribution control element 5 and corresponding to a transmittance distribution and a phase distribution is formed on the wafer 1 by the focusing lens 6. When a cylindrical lens is used as the focusing lens 6, the cylindrical lens transmits the light of the illumination intensity distribution image in the direction of one of its optical axes and focuses a laser beam (illumination light) in the direction of another one of the optical axes to allow the illumination intensity distribution (provided by the illumination intensity distribution control element 5 and corresponding to the transmittance distribution or the phase distribution) to be projected in the scanning direction S2 and allow an area having a small length in the scanning direction S1 to be illuminated. A distribution of illumination intensities of the laser beam emitted by the laser source 2 is represented by a substantial Gaussian distribution. When the defect inspection apparatus does not cause the illumination intensity distribution control element 5 to act, the laser beam that exhibits a Gaussian distribution and is shaped by the beam expander 7 and the focusing lens 6 is projected on the wafer 1.

As the illumination intensity distribution control element 5 having the fixed transmittance distribution or the fixed phase distribution, a diffractive optical element (DOE), a homogenizer (aspheric lens, micro lens array, optical fiber bundle, or hollow pipe having an inner surface coated by reflective coating) or the like may be used. When the illumination intensity distribution control element 5 is composed of a dynamically variable spatial light modulator (SLM) that is controlled by the controller 14 connected with the overall control unit 53, the shape of the illumination intensity distribution is dynamically controlled (adjusted) before and after the scanning of the illumination area 20 of the wafer 1 or during the scanning of the illumination area 20 of the wafer 1. The dynamically variable spatial light modulator of transmission type is a liquid crystal element, a magneto-optical spatial light modulator or the like. The dynamically variable spatial light modulator of reflection type is a digital micromirror device (DMD), a grating light valve (GLV), a reflection-type liquid crystal element (such as a liquid crystal on silicon (LCOS)) or the like.

FIGS. 6A to 6C are diagrams each showing an example of the illumination intensity distribution formed by the illumination optical system 101 having the aforementioned configuration. FIG. 6A shows a substantial Gaussian distribution that indicates the distribution of the illumination intensities of the laser beam emitted by the laser source 2. FIG. 6B shows a uniform illumination intensity distribution obtained when the homogenizer or the like is used as the illumination intensity distribution control element 5. The uniform illumination intensity distribution shown in FIG. 6B is suitable to suppress thermal damage to the wafer due to illumination with a laser beam having a high intensity and to maximize the amount of light scattered from a defect and thereby perform high-sensitivity inspection. FIG. 6C shows an illumination intensity distribution dropped an intensity of a central portion compared with the uniform illumination intensity distribution. The temperature rise generated when the uniform illumination intensity distribution is formed becomes the maximum at a central portion of the illumination intensity distribution. Thus, thermal damage may occur at the central portion of the illumination intensity distribution to the wafer. The illumination intensity distribution shown in FIG. 6C is suitable to avoid the thermal damage to the central portion of the illumination intensity distribution and detect the light with high sensitivity.

Next, the signal processor 105 according to the present invention is described below. The signal processor 105 is adapted to classify various types of defects and estimate the sizes of the defects based on signals indicating the intensities of the light detected by the detection optical units (covering a wide angular range).

First, an analog processor 51 included in the signal processor 105 is described below with reference to FIG. 7. The description below is made of the analog processor 51 that is connected with the two detection optical units 102a and 012b for simplicity. The analog processor 51 includes pre-amplifiers 501a, 502b, low pass filters 511a, 511b, and analog-digital (A/D) converters 502a, 502b. The light detectors 9a and 9b output signal currents to the pre-amplifiers 501a, 502b, respectively. The signal currents output from the light detectors 9a and 9b are converted into voltages (analog signals) by the pre-amplifiers 501a and 502b, respectively. The pre-amplifiers 501a and 502b then amplify the voltages. The low pass filters 511a, 511b remove high frequency noise components from the amplified analog signals. The A/D converters 511a, 511b has sampling rates sufficiently higher than cut-off frequencies of the low pass filters 511a, 511b. After the low pass filters 511a, 511b remove the high frequency noise components, the A/D converters 511a, 511b convert the analog signals into digital signals and output the digital signals to a digital processor 52, respectively.

Figure 8:
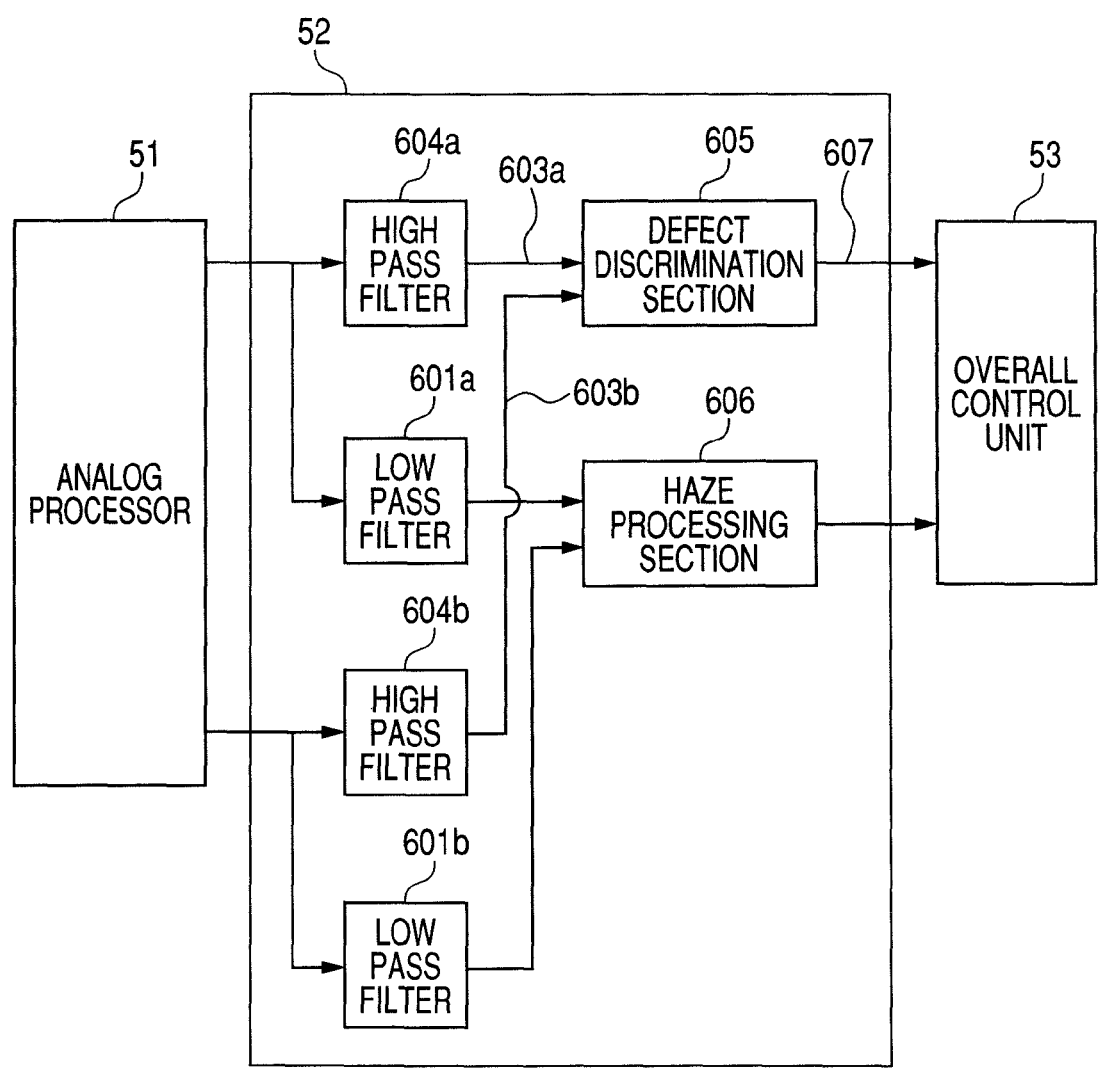
FIG. 8 is a block diagram showing a digital processor included in the signal processor.

Next, the digital processor 52 included in the signal processor 105 is descried below with reference to FIG. 8. The signals output from the analog processor 51 are received by high pass filters 604a, 604b included in the digital processor 52. The high pass filters 604a, 604b extract defect signals 603a, 603b from the received signals and output the defect signals 603a, 603b to a defect determination section 605 included in the digital processor 52. The defect determination section 605 receives the defect signals 603a, 603b. Since a defect is scanned in the illumination area 20 in the scanning direction S1, the waveform of each of the defect signals is obtained by enlarging or reducing an illumination intensity distribution profile (of the laser beam with which the area 20 is illuminated) in the scanning direction S1. The high pass filters 604a, 604b pass signals having frequencies within a frequency band that includes frequencies of the defect signals. The high pass filters 604a, 604b remove signals of a frequency band that includes a relatively large amount of noise and remove a direct current component that includes a relatively large amount of noise. Therefore, the high pass filters 604a, 604b improve the signal-to-noise ratios of the defect signals 603a, 603b, respectively. As the high pass filters 604a, 604b, the following filters may be used: a high pass filter having a specified cut-off frequency and designed to shield a component having a frequency equal to or higher than the cut-off frequency; a band pass filter having a specified cut-off frequency and designed to shield a component having a frequency equal to or higher than the cut-off frequency; a finite impulse response filter designed to pass a signal having a waveform similar to those of the defect signals. The defect determination section 605 performs threshold processing on the defect signals output from the high pass filters 604a, 604b to determine whether or not a defect is present. Specifically, the defect determination section 605 receives the defect signals that are based on the signals detected by the detection optical units. The defect determination section 605 can perform threshold processing on the sum or weighted average of the defect signals, or perform OR logical calculation or AND logical calculation on a defect group extracted by the threshold processing performed on the defect signals by means of coordinates set on the top surface of the wafer, to inspect the defect with high sensitivity compared with defect inspection using a single defect signal.

The defect determination section 605 calculates estimated positional coordinates (indicating the position of a defect on the wafer) and an estimated size of the defect based on the waveform of a defect signal (obtained from a location at which the defect is determined to be present) and a sensitivity information signal (obtained from the location at which the defect is determined to be present). The defect determination section 605 transmits, to the overall control unit 53, the estimated positional coordinates and the estimated size of the defect. The estimated positional coordinates and the estimated size of the defect are transmitted as defect information 607. The estimated positional coordinates indicating the position of the defect is calculated based on the barycenter of the waveform of the defect signal. The estimated size of the defect is calculated based on a value obtained by integrating the waveform of the defect signal.

The signals output from the analog processor 51 are also received by low pass filters 601a, 601b, respectively. The low pass filters 601a, 601b are included in the digital processor 52. The low pass filters 601a, 601b output, to a haze processor 606, low-frequency components and direct current components, which correspond to the amount of light (haze) scattered from extremely small roughness present in the illumination area 20 on the wafer 1. The haze processor 606 receives the low-frequency components and the direct current components and performs processing on the received components to obtain haze information. The haze processor 606 outputs a haze signal corresponding to the intensity of the haze for each location on the wafer based on the values of the signals received from the low pass filters 601a, 601b. An angular distribution of light scattered from the roughness of the wafer varies depending on a spatial frequency distribution of extremely small roughness. As shown in FIG. 8, haze signals are transmitted from the light detectors 9 of the detection optical units 102 (located in different directions and at different angles with respect to the top surface of the wafer) to the haze processor 606. Therefore, the haze processor 606 can output information related to the spatial frequency distribution of the extremely small roughness based on the ratio(s) of the intensities of the haze signals.

When a part of the laser beam reaches a convex part of the edge portion of the wafer, light is diffracted from the convex part. The diffracted light has a high intensity. The diffracted light is incident on the light detectors 9 of the detection optical units 102 that covers a large solid angle. The light detectors 9 are therefore saturated. As a result, the defect inspection apparatus cannot perform the inspection. In addition, the light detectors 9 may be degraded or damaged since the light detectors 9 receive a large amount of light. Light may be diffracted depending on the shape of a grip that holds the wafer at the edge portion of the wafer. In this case, the diffracted light has a high intensity.

According to the present invention, one or more of the detection optical unit(s) 41 and the signal processor 105 as shown in FIG. 11 monitor the intensity of light diffracted from the edge portion of the wafer in the process for inspecting a defect present near the edge portion of the wafer. Only the light detector(s) of the detection optical unit(s) 41, to which the light diffracted from the edge portion propagates, is set to shield light. The light detectors 9 of the other detection optical units 102, which do not need to shield light, are set to detect light from the top surface of the wafer (including a wafer portion located near the edge portion of the wafer) with high sensitivity. A failure (attachment of a foreign material, peeling of a film, or the like) may easily occur at the wafer portion located near the edge portion of the wafer. This configuration of the apparatus can maximize the total area of a chip(s) that is included in the total area of the wafer and can be used as a good product(s). Therefore, the yield of the chip(s) is improved. Next, the configuration of the defect inspection apparatus, which is a feature of the present invention, is described below with reference to the accompanying drawings.

Figure 9A:
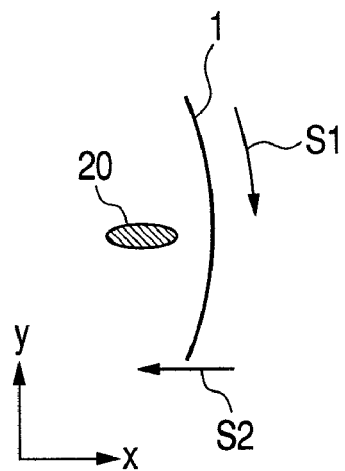
FIG. 9A is a plan view of the wafer and shows an illumination area located near an edge portion of the wafer by scanning in a direction S1 and a direction S2.
Figure 9B:
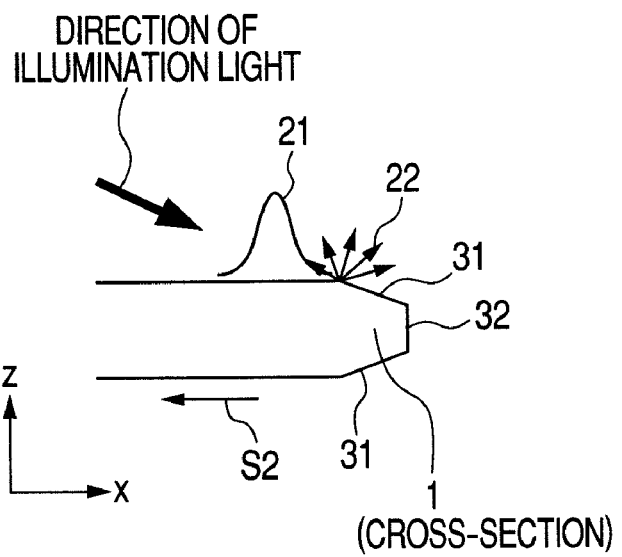
FIG. 9B is a cross sectional view of the wafer in the case where the illumination area is located near the edge portion of the wafer.
Figure 9C:
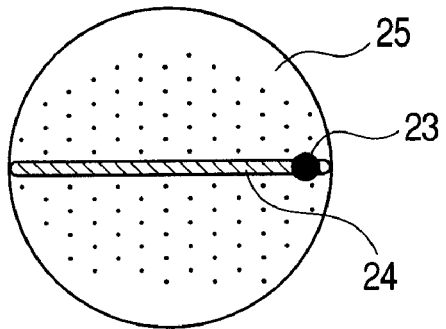
FIG. 9C is a plan view of the wafer and shows light diffracted from the edge portion of the wafer and light scattered from the edge portion of the wafer.

First, a description is made of light diffracted from the edge portion of the wafer and light scattered from the edge portion of the wafer in the case where the illumination area 20 according to the present invention is located near the edge portion of the wafer and scanned, with reference to FIGS. 9A and 9B. FIG. 9A shows the illumination area 20 when viewed from a top side of the wafer. The illumination area 20 is scanned from the center of the top surface of the wafer 1 in the scanning directions S1 and S2. In FIG. 9A, the illumination area 20 is present near the edge portion of the wafer 1. FIG. 9B shows a cross section of the wafer 1 in the case where the illumination area 20 is present near the edge portion of the wafer 1. The edge portion of the wafer 1 has inclination parts (upper and lower inclination parts) 31 and a side surface 32. Each of the upper and lower inclination parts 31 is generally called a bevel. The upper inclination part 31 is called an upper bevel herein. The side surface 32 is generally called an apex. It is assumed that an illumination intensity distribution 21 of the laser beam is a Gaussian distribution. The illumination intensity distribution 21 is schematically illustrated in FIG. 9B. When an end portion (low intensity part) of the illumination intensity distribution 21 is present near the edge portion of the wafer, light 22 is scattered and diffracted from the edge portion, especially from an angle portion of boundary between the upper bevel of the edge portion and the top surface of the wafer. The light 22 has a higher intensity than that of light scattered from small roughness having a size of one nanometer to several angstroms present on the top surface of the wafer. This is because a ruggedness scale of the angle portion of the bevel part boundary is extremely large more than micron order (one micrometer to several micrometers) compared with the small roughness having a size of one nanometer to several angstroms. Thus, the ruggedness scale is significantly larger than the small roughness. An angular distribution of the light scattered and diffracted from the edge portion is schematically illustrated in FIG. 9C. FIGS. 9A to 9C are drawn based on the method for illustrating azimuths and angles that are used for the detection optical unit described with reference to FIG. 4A. The line of the boundary between the upper bevel of the edge portion and the top surface of the wafer is perpendicular to the direction of propagation of the illumination light (laser beam) due to the spiral scanning performed by means of the scanning in the circumferential direction S1 and the scanning in the translational direction S2. Therefore, light 24 is diffracted from the edge portion in the direction of incidence of the illumination light on the top surface of the wafer, in the direction 23 of propagation of light specularly reflected and in the direction toward the apex of the hemisphere, as shown in FIG. 9C. Light 25 is scattered around the diffracted light 24 due to the boundary between the upper bevel of the edge portion and the top surface of the wafer and due to roughness of the bevel as shown in FIG. 9C.

When the diffracted light 24 is directly incident on the light detector 9 of the detection optical unit 102, the light detector 9 may be degraded or damaged. This is because the diffracted light 24 has a high intensity.

Figure 10A:
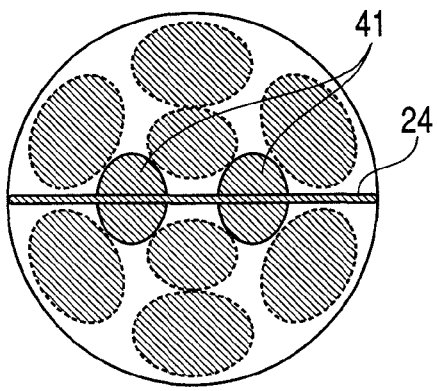
FIG. 10A is a plan view of detection optical units in the case there the light diffracted from the edge portion is incident on some of the detection optical units.

A method for avoiding the degradation and damage of the light detector 9, which is a feature of the present invention, is described below with reference to FIGS. 10A to 11.

Figure 10B:
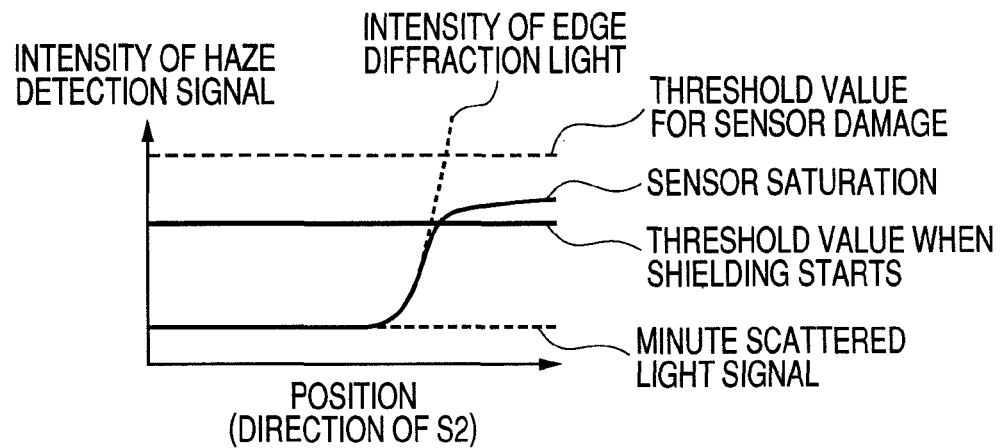
FIG. 10B is a graph showing the relationship between the position (of a portion of the wafer) in a radial direction of the wafer and a signal indicating the intensity of the light diffracted from the edge portion in the case where a distribution of intensities of illumination light is represented by a Gaussian distribution.
Figure 10C:
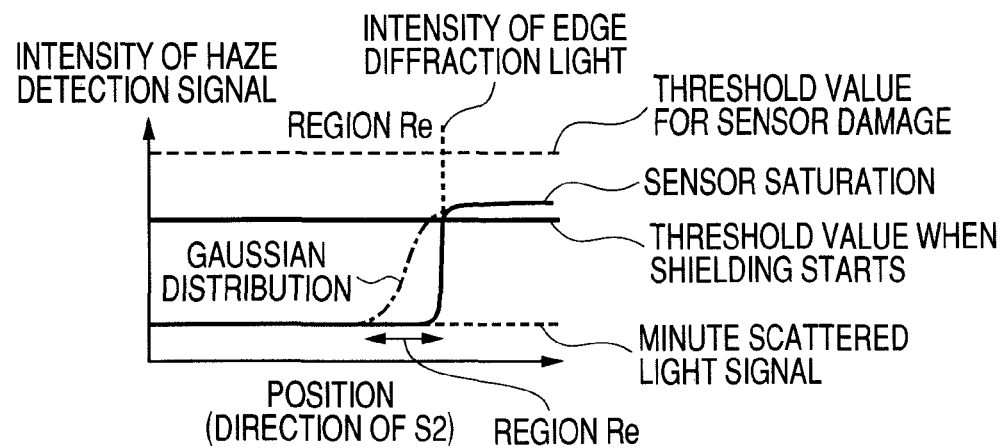
FIG. 10C is a graph showing the relationship between the position (of a portion of the wafer) in the radial direction of the wafer and a signal indicating the intensity of the light diffracted from the edge portion in the case where a distribution of intensities of illumination light is uniform.

First, a system (composed of the detection optical unit(s) 41 and the signal processor 105) for monitoring the intensity of the light diffracted from the edge portion of the wafer is described below with reference to FIGS. 10A to 10C. The detection optical units 102 are arranged in the same manner as the arrangement described with reference to FIG. 4B1. As shown in FIG. 10A, the light 24 diffracted from the edge portion is incident on some of the detection optical units. The detection optical units that receive the diffracted light 24 are hereinafter denoted by reference numeral 41. As a result, the light detectors 9 of the detection optical units 41 detect signals, respectively. The detected signals passes through the analog processor 51 and are received by the low pass filters 601 included in the digital processor 52. Then, the low pass filters 601 output diffracted light intensity signals (each of which indicates the intensity of the light diffracted from the edge portion) shown in FIGS. 10B and 10C. FIG. 10B shows the case where the illumination intensity distribution of the illumination light (laser beam) is a Gaussian distribution, while FIG. 10C shows the case where the illumination intensity distribution of the illumination light (laser beam) is uniform (and includes a rapid reduction in the illumination intensity at a location distant from the center of a spot of the laser beam incident on the top surface of the wafer). Since the illumination intensity distribution shown in FIG. 10B is a Gaussian distribution, the intensity of the diffracted light intensity signal shown in FIG. 10B increases as the illumination area 20 approaches the edge portion of the wafer 1. On the other hand, since the illumination intensity distribution shown in FIG. 10C is uniform, the intensity of the diffracted light intensity signal shown in FIG. 10C rapidly increases as the illumination area 20 approaches the edge portion of the wafer. The speed of the scanning in the translational direction S2 (radial direction of the wafer) is lower than the speed of the scanning in the circumferential direction S2. Thus, the intensity of the diffracted light intensity signal (shown in FIG. 10C) gradually changes with respect to time. For example, the haze processor 606 can monitor the diffracted light intensity signals by monitoring haze signals output from the detection optical units 41, i.e., by monitoring signals output from the low pass filters 601. Thus, the haze processor 606 determines whether or not the intensity of the haze signal output from each of the detection optical units 41 is higher than a predetermined threshold for triggering shielding of light, for example. When the intensity of the haze signal output from the detection optical unit 41 is higher than the predetermined threshold, a light shielding unit (shown in FIG. 11 and described later) shields the light diffracted from the edge portion and having a high intensity to prevent the light from being incident on the light detectors 9 of the detection optical units 102. This can prevent the light detectors 9 from being damaged due to the light diffracted from the edge portion.

In the uniform illumination intensity distribution (of the illumination light) shown in FIG. 10C, an illumination intensity at a location distant from the center of the spot of the laser beam incident on the top surface of the wafer is lower than that in the Gaussian distribution (indicated by an alternate long and short dash line shown in FIG. 10C). Thus, the light diffracted from the edge portion and the light scattered from the edge portion have low intensities in a region Re that is located near the edge portion. Therefore, when the illumination intensity distribution of the illumination light is uniform, high-sensitivity inspection can be performed on the region Re in a similar manner as the inspection performed on the top surface of the wafer.

The light shielding unit (light blocking unit) included in the detection optical unit 41 is described below with reference to FIG. 11. The detection optical unit 41 is configured by adding a light shielding shutter (light blocking shutter) 15 to the configuration of the detection optical unit 120. A light shielding shutter controller 16 transmits an electrical switch signal to the light shielding shutter 15 based on a diffracted light intensity signal monitored by the digital processor 52 and determined that the signal has an intensity higher than the predetermined threshold for triggering shielding of light. The light shielding shutter 15 is switched to a light shielding state or to a light transmission state based on the electrical switch signal received from the light shielding shutter controller 16. When the light shielding shutter 15 is switched to the light shielding state, the light shielding shutter 15 shields the laser beam. When the light shielding shutter 15 is switched to the light transmission state, the light shielding shutter 15 transmits the laser beam. As the light shielding shutter 15, a mechanical shutter, a liquid crystal filter, an electrooptical element, an acoustooptic element or the like may be used. The light shielding shutter controller 16 receives, from the digital processor 52, a determination signal indicating whether or not the intensity of the light diffracted from the edge portion is higher than a certain intensity value. When the intensity of the light diffracted from the edge portion is higher than the certain intensity value, the light shielding shutter controller 16 transmits, to the light shielding shutter 15, a signal instructing the light shielding shutter 15 to be set to the light shielding state. Only the detection optical unit(s) 41 having the aforementioned configuration(s) can shield the light to protect the light detector(s) 9. Each of the detection optical unit(s) 41 would receive an excessive amount of the light diffracted from the edge portion if the detection optical unit 41 did not have the light shielding shutter 15.

Figure 12A:
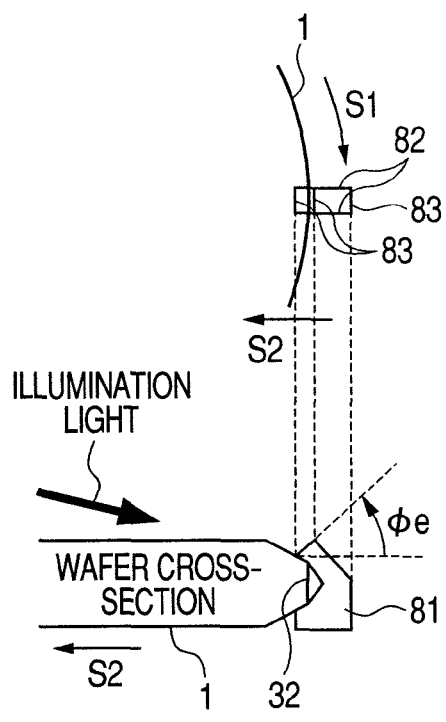
FIG. 12A is a cross sectional view and plan view of the wafer and an edge grip that holds the wafer.

Next, an edge grip according to the present invention is described below with reference to FIGS. 12A to 12D. The edge grip is adapted to hold the wafer. An edge chuck is used to press the edge portion from the opposite side of the wafer and thereby hold the wafer in order to prevent a back surface of the wafer from being contaminated and prevent a foreign material from being attached to the back surface of the wafer. A part of the edge chuck, which contacts and holds the edge portion of the wafer, is called the edge grip. The edge grip is denoted by reference numeral 81. FIG. 12A shows the edge grip 81 when viewed from a top side of the edge grip 81. FIG. 12A also schematically illustrates a cross section of the edge grip 81. The edge grip 81 has a side (ridge) extending in a direction substantially parallel to the scanning direction S1, i.e., the circumferential direction of the wafer. This side of the edge grip 81 is indicated by a bold line shown in FIG. 12A. The side of the edge grip 81 is regarded as an edge grip ridge 83. The edge grip 81 also has a side (ridge) extending in a direction substantially parallel to the scanning direction S2, i.e., the radial direction of the wafer. This side of the edge grip 81 is regarded as an edge grip ridge 82. An angle formed between the top surface of the wafer and a surface (on which the illumination light is incident) of the edge grip, i.e., an angle formed between the top surface of the wafer and the edge grip ridge 82, is indicated by φe. As shown in FIG. 12A, a portion of the edge grip 81 is located on the side of a central portion of the wafer with respect to the apex 32. Thus, light diffracted and scattered from the edge grip 81 may disturb high-sensitivity inspection on a wafer portion located near the edge portion.

Figure 12B:
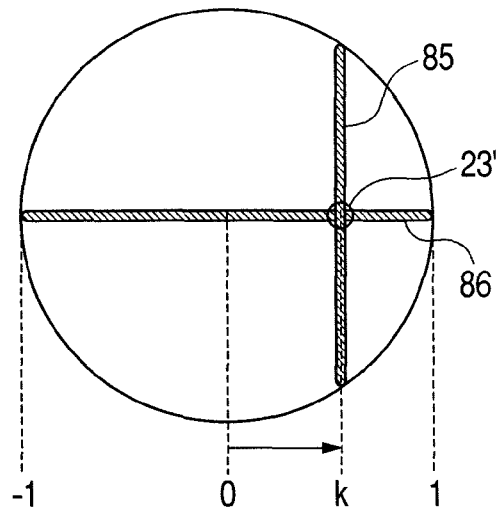
FIG. 12B is a plan view of the wafer and shows light diffracted from the edge grip.

When the illumination area 20 is present near the edge portion of the wafer, light is diffracted and scattered from the edge grip 81 in a similar manner to the light diffracted and scattered from the edge portion. In the case where the surface (on which part of the illumination light is incident) of the edge grip 81 and the edge grip ridges 82, 83 are ground to reduce irregularities, intensities of light scattered from the edge grip 81 are lower than those of light diffracted from the edge grip 81. Thus, light 85 and 86 diffracted from the edge grips 82, 83 is dominant among light generated from the edge grip 81. FIG. 12B illustrates directions of propagation of the light 85, 86 diffracted from the edge grip ridges 82, 83 based on of the method (described with reference to FIG. 4A) for illustrating azimuths and angles that are used for the detection optical unit. The edge grip ridge 83 extends in the same direction as that of extension of the boundary between the bevel of the edge portion and the top surface of the wafer of the bevel. Thus, the light 86 diffracted from the edge grip ridge 83 propagates in the direction of the incidence of the illumination light, in the direction 23' of the propagation of the light specularly reflected on the surface of the edge grip, and in the direction toward the apex of the hemisphere. On the other hand, the edge grip ridge 82 extends in a direction perpendicular to the direction of extension of the edge grip ridge 83. Thus, the light 85 diffracted from the edge grip ridge 82 propagates through the path of the propagation of the specularly reflected light and in a direction perpendicular to the direction of the propagation of the light 86 diffracted from the edge grip ridge 83. A distance between the center of the top surface of the wafer and an edge of the wafer is regarded as 1. This distance means a distance between the apex of the hemisphere and a point crossing the following two lines: a line that is parallel to the top surface of the wafer and extends from the apex of the hemisphere; and a line that is parallel to the normal to the top surface of the wafer and extends from the edge of the wafer. The following distance is indicated by k: a distance between the apex of the hemisphere and a point crossing the direction 23' of the propagation of the light specularly reflected on the surface of the edge grip 81 and the line that is parallel to the top surface of the wafer and extends from the apex of the hemisphere. The direction of the propagation of the light 85 diffracted from the edge grip ridge 82 is determined by the distance k. The distance k is calculation by the following formula. When the angle of the incidence of the illumination light on the surface of the edge grip 81 with respect to the normal to the top surface of the wafer is indicated by φi, an angle at which the light specularly reflected on the surface of the edge grip is indicated by a value of (φi−2φe). In accordance with the definition shown in FIG. 4A, k=sin (φi−2φe). Therefore, the distance k, which determines the direction of the diffracted light 85, can be selected based on the shape (e.g., the angle φe or the like) of the edge grip 81 and the incident angle φi of the illumination light.

Figure 12C:
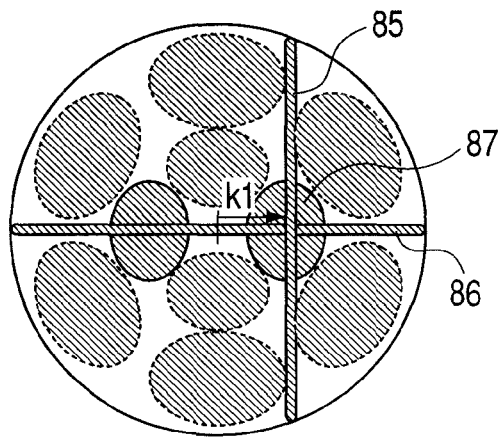
FIG. 12C is a plan view of detection optical units in the case where a distance k is selected to be a value k1 that minimizes the number of the detection optical units receiving the light diffracted from the edge grip.

FIG. 12C shows the case where the distance k is set to a distance k1 that minimizes the number of the detection optical units receiving the light diffracted from the edge grip ridges. As shown in FIG. 12C, the diffracted light 85 is incident on only a detection optical unit 87. The detection optical unit 87 receives the light 24 (shown in FIG. 9C) diffracted from the edge portion and the light 85 (shown in FIG. 12B) diffracted from the edge grip ridge 82 (The detection optical units 41 include the detection optical unit 87). The detection optical units 41 selectively shield (block) the light diffracted from the edge portion and the edge grip by means of the light shielding units shown in FIGS. 10A to 11 to prevent the light detectors 9 of the detection optical units 41 from being damaged. In this case, the other detection optical units 102 are capable of detecting a defect.

Figure 12D:
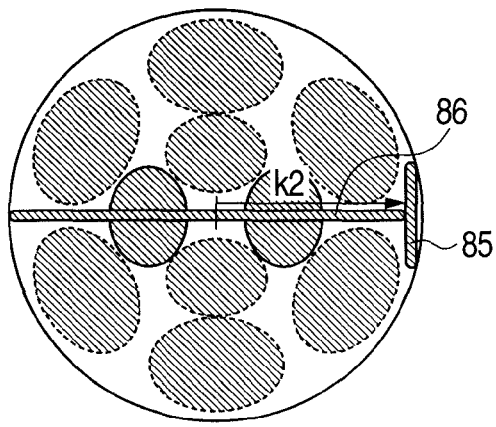
FIG. 12D is a plan view of the detection optical units in the case where the distance k is selected to be a value k2 that results in the fact that the light diffracted from the edge grip is not incident on any of the detection optical units.

FIG. 12D shows the case where the distance k is set to a distance k2 that prevents the diffracted light 85 from being incident on any of the detection optical units. In the case shown in FIG. 12D, it is effective to increase the incident angle φi of the illumination light (i.e., to perform illumination at a low elevation angle) and reduce the angle φe (i.e., to set the surface (on which the illumination light is incident) of the edge grip to be nearly parallel to the top surface of the wafer). In order to prevent the diffracted light 85 from being incident on any of the detection optical units, it is necessary that the distance k2 be, for example, larger than 0.95. In order to set the distance k2 to be larger than 0.95, it is necessary that the value of (φi−2φe) be larger than 72 degrees. Thus, it is necessary to use an edge grip satisfying the following requirements: when φi=70 degrees, φe<−1 degree; and when φi=80 degrees, φe<4 degrees. The incident angle φi of the illumination light may be set based on the shape of the edge grip 81.

As described above, the defect inspection apparatus is capable of preventing the light detectors of the detection optical units 41 from being damaged and of detecting, with high sensitivity, a defect present in a wide area that includes a wafer portion located near the edge portion and a wafer portion located near the edge grip. Thus, the defect inspection apparatus is capable of maximizing the total area of a chip(s) that is included in the total area of the wafer and can be used as a good product(s) to improve the yield of the product(s).

Figure 13A:
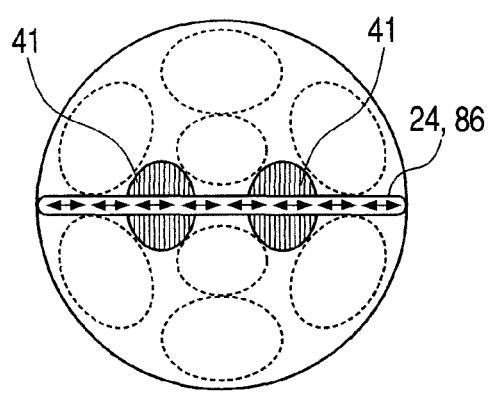
FIG. 13A is a plan view of the detection optical units and shows polarization states of light diffracted from the edge portion and the edge grip in the case where illumination is performed with a P-polarized laser beam.
Figure 13B:
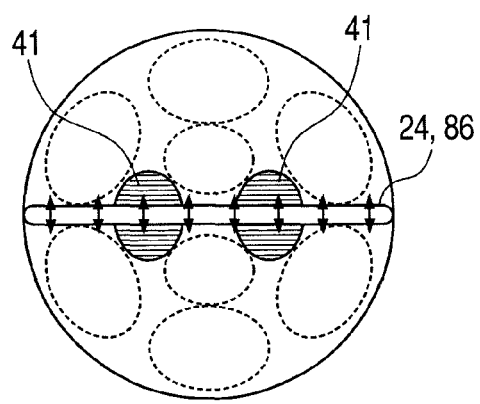
FIG. 13B is a plan view of the detection optical units and shows polarization states of light diffracted from the edge portion and the edge grip in the case where illumination is performed with an S-polarized laser beam.

Next, a description is made of an analyzer (polarizing filter) for removing the light 24 diffracted from a wafer portion located near the edge portion of the wafer and incident on a detection optical unit 41 and the light 86 diffracted from the edge grip 81 (that presses the edge portion of the wafer to hold the wafer) and incident on any of the detection optical units 41 (including the detection optical unit 87) with reference to FIG. 13.

In order to detect an extremely small defect present on small roughness of the wafer, the illumination optical system 101 illuminates the wafer 1 with a P-polarized laser beam from a direction oblique to the normal to the top surface of the wafer 1. An electric field is generated by the illumination with the P-polarized light from the oblique direction. A plane including the incident direction of the illumination light and the direction of the normal to the top surface of the wafer is regarded as an incident plane of the illumination light. The electric field oscillates only in a direction parallel to the incident plane. Thus, the light diffracted and scattered in the incident plane oscillates in the direction (left-right direction of FIG. 13A) parallel to the incident plane. When each of the detection optical units 41 (including the detection optical unit 87) uses a polarizing filter capable of shielding light having a polarization direction parallel to the incident plane, the detection optical units 41 (including the detection optical unit 87) can shield the diffracted light 24 and the diffracted light 86.

In order to detect a defect present on relatively coarse roughness of the wafer, the illumination optical system 101 shown in FIG. 1 uses an S-polarized laser beam as the illumination light to illuminate the roughness with the S-polarized laser beam from a direction oblique to the normal to the top surface of the wafer. In the case where the wafer is illuminated with the S-polarized laser beam, the polarization direction (top-bottom direction of FIG. 13B) of the light 24 diffracted from the edge portion of the wafer and the polarization direction (top-bottom direction of FIG. 13B) of the light 86 diffracted from the edge grip 81 are perpendicular to the polarization direction of the light 24 diffracted from the edge portion due to the illumination with the P-polarized laser beam from the oblique direction and to the polarization direction of the light 86 diffracted from the edge grip 81 due to the illumination with the P-polarized laser beam from the oblique direction. When the detection optical unit 41 uses a polarizing filter 13 capable of shielding light having the polarization direction (parallel to that of light 24, 86 diffracted due to the illumination with the S-polarized laser beam), the detection optical unit 41 can shield the light 24 diffracted from the edge portion of the wafer due to the illumination with the S-polarized laser beam and the light 86 diffracted from the edge grip 81 due to the illumination with the S-polarized laser beam.

As described above, each of the detection optical units 41 (including the detection optical unit 87) has the polarizing filter (analyzer) 13 to detect an extremely small defect present on fine roughness of the wafer and detect a defect present on relatively coarse roughness of the wafer. The polarizing filter (analyzer) 13 is set in a crossed nicols state with respect to the polarization of the illumination light. Accordingly, each of the detection optical units 41 (including the detection optical unit 87) can selectively shield (block) the light 24 diffracted from the edge portion and the light 86 diffracted from the edge grip 81. In this case, after light scattered from a defect passes through the polarizing filter 13, each of the detection optical units 41 (including the detection optical unit 87) detects the light scattered from the defect. This is because the polarization state of the light scattered from the defect is disturbed depending on the shape and material of the defect. Each of the other detection optical units does not include the analyzer (polarizing filter) 13. Thus, each of the other detection optical units can detect a defect in a wide area extending from a wafer portion located near the edge portion to a wafer portion located near the edge grip.

Figure 14:
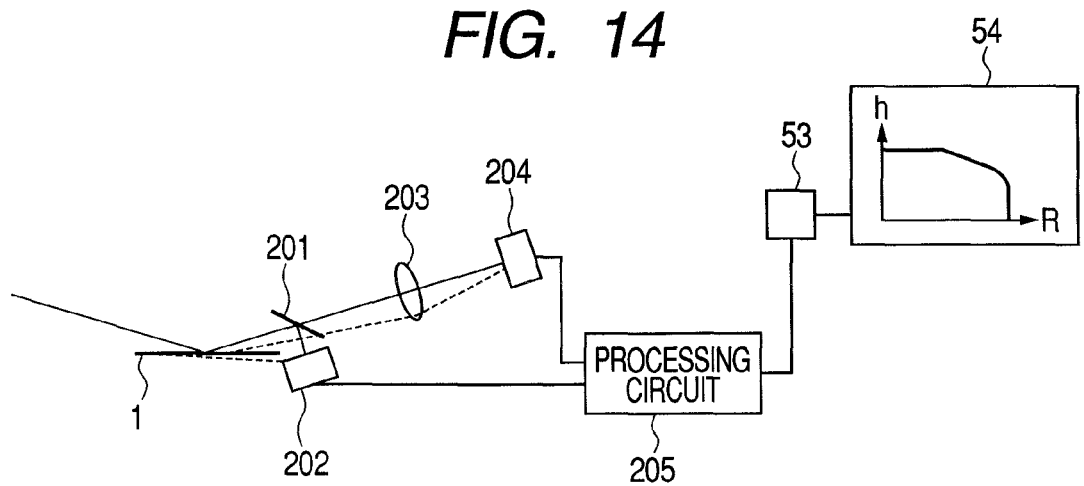
FIG. 14 is a diagram showing the configuration of a unit (wafer cross sectional profile measurement unit) for measuring displacement of the illumination area.
Figure 15:
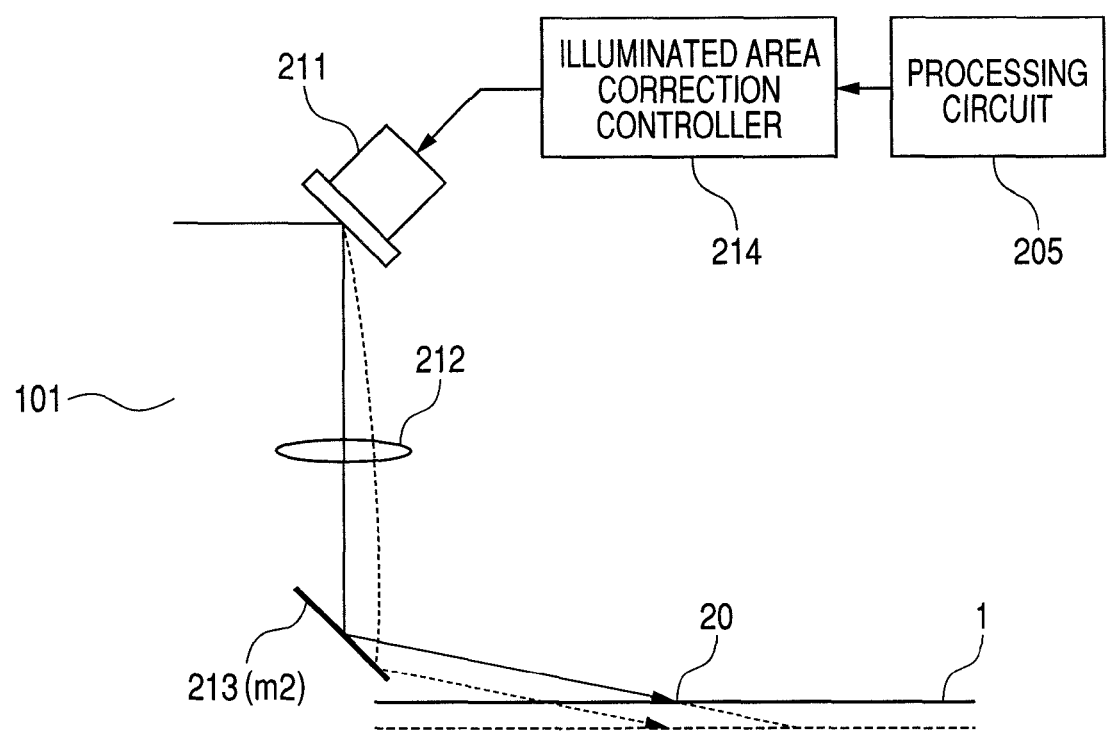
FIG. 15 is a diagram showing the configuration of a unit for correcting the position of the illumination area.

Next, a description is made of a unit (wafer cross sectional profile measurement unit) for measuring displacement of an illumination area and a unit for correcting the position of the illumination area with reference to FIGS. 14 and 15. These two units are used to correct the position of the illumination area displaced due to displacement (displacement of an inclination angle of the top surface and displacement of the vertical position of the top surface of the wafer) of the top surface of the wafer. The two units prevent the illumination area from being present outside a field of view of the detection optical unit and prevent the inspection sensitivity to be reduced. FIG. 14 is a diagram showing the outline configuration of the illumination area displacement measurement unit (wafer cross sectional profile measurement unit) according to the present invention. FIG. 15 is a diagram showing the outline configuration of the illumination area position correction unit according to the present invention. An angle of the direction of propagation of the illumination light specularly reflected on the top surface of the wafer with respect to the normal to the top surface of the wafer and the position of a wafer portion on which the illumination light is specularly reflected vary depending on the inclination angle of the top surface of the wafer and on the vertical position of the top surface of the wafer. The illumination area displacement measurement unit (wafer cross sectional profile measurement unit) has a focusing lens 203, a position detector 204, a half mirror 201, a position detector 202 and a processing circuit 205. The focusing lens 203 has a focal length f as shown in FIG. 14. The focusing lens 203 is located on an optical path of the illumination light specularly reflected. Also, the focusing lens 203 is separated from the top surface of the wafer by a distance sufficiently larger than the focal length f. The position detector 204 is located to ensure that a distance between a detection surface of the position detector 204 and the focusing lens 203 is equal to the focal length f. The position detector 204 is adapted to detect, as positional displacement, displacement of the angle at which the light is specularly reflected on the top surface of the wafer with respect to the normal to the top surface of the wafer due to displacement of the inclination angle of the top surface of the wafer and due to displacement of the vertical position of the top surface of the wafer. The position detector 202 is located on an optical path of the light specularly reflected and deflected by the half mirror 201. The position detector 202 is adapted to detect displacement of the angle at which the light is specularly reflected on the top surface of the wafer with respect to the normal to the top surface of the wafer and displacement (i.e., displacement of the illumination area 20) of the location at which the light is specularly reflected on the top surface of the wafer. The processing circuit 205 performs processing to subtract the displacement (detected by the position detector 204) of the angle at which the light is specularly reflected on the top surface of the wafer with respect to the normal to the top surface of the wafer from the displacement (detected by the position detector 202) of the angle at which the light is specularly reflected on the top surface of the wafer with respect to the normal to the top surface of the wafer and the displacement of the illumination area 20 to calculate the displacement of the illumination area 20. The processing circuit 205 transmits a signal indicating the displacement of the illumination area 20 to the overall control unit 53. The overall control unit 53 receives the signal from the processor circuit 205 and divides the displacement of the illumination area 20 by $\sin(\phi i)$ to convert the displacement of the illumination area 20 into displacement of the vertical position of the top surface of the wafer. The overall control unit 53 stores the displacement of the vertical position of the top surface of the wafer for each scanned region R defined in the scanning direction (translational direction) S2 to obtain the profile of the cross section of an wafer portion extending from the top surface to the edge portion. The profile obtained by the overall control unit 53 is displayed by the display unit 54 as a graph.

When the illumination area 20 is displaced due to displacement of the vertical position of the top surface of the wafer and thereby present outside the field of view of any of the detection optical units, the inspection sensitivity is reduced. To avoid this, it is necessary to correct the position of the illumination area by means of the illumination area position correction unit based on the displacement (measured by the illumination area displacement measurement unit (wafer cross section profile measurement unit)) of the illumination area 20. The illumination area position correction unit included in the illumination optical system 101 has a beam deflecting element 211, a focusing lens 212 and a mirror 213(m2) on an optical path of the illumination optical system 101. The beam deflecting element 211 controls the direction of the propagation of the illumination light. Then, the illumination light is reflected on the mirror 213(m2) and introduced onto the wafer 1. An illumination area position correction controller 214 controls the beam deflecting element 211 to adjust the degree of the deflection of the illumination light and thereby adjust the direction of the propagation of the illumination light. In addition, the illumination area position correction controller 214 controls the beam deflecting element 211 based on the measured displacement (transmitted from the processing circuit 205 (including the overall control unit 53)) of the illumination area 20 to place the illumination area 20 at its original location. Thus, the position of the illumination area 20 with respect to an angular range in which scattered light is detected by each of the detection optical units is corrected for the displacement of the inclination angle of the top surface of the wafer (including a wafer portion located near the edge portion) and the displacement of the vertical position of the top surface of the wafer (including a wafer portion located near the edge portion). That is, the angle of the direction of the propagation of the specularly reflected light with respect to the normal to the top surface of the wafer and the location at which the light is specularly reflected (for example, the direction 23 of propagation of light specularly reflected and the direction 23' of the propagation of the light specularly reflected on the surface of the edge grip 81) are corrected for the displacement of the inclination angle of the top surface of the wafer (including a wafer portion located near the edge portion) and the displacement of the vertical position of the top surface of the wafer (including a wafer portion located near the edge portion). As a result, the detection optical unit(s) 41 (including the detection optical unit 87) shields (blocks) the light 24 diffracted from the edge portion and the light 86 diffracted from the edge grip 81, while the other detection optical units do not receive the diffracted light 24, 86 and detect light scattered in a wide angular range to inspect the top surface of the wafer and a wafer portion located near the edge portion of the wafer with high sensitivity.

According to the embodiment of the present invention, the defect inspection apparatus has the wafer cross sectional profile measurement unit and the illumination area position correction unit to correct displacement of the illumination area due to displacement (displacement of the inclination angle and the displacement of the vertical position) of the top surface of the wafer, i.e., due to displacement of the angle at which the illumination light is specularly reflected on the top surface of the wafer with respect to the normal to the top surface of the wafer, and displacement of the position of the wafer portion on which the illumination light is specularly reflected (for example, the direction 23 and the direction 23'). The specified detection optical unit(s) shields (blocks) the light diffracted from the edge portion and the light diffracted from the edge grip, while the other detection optical units can cover a wide angular range by means of the light detectors and increase the inspection sensitivity by setting focal depths to be small and increasing spatial resolutions. According to the embodiment of the present invention, the illumination optical system 101 scans the wafer with an extremely laser beam spot, and the plurality of detection optical units 102 detects light scattered at a large solid angle with a high efficiency of converging light. Therefore, the defect inspection apparatus is capable of inspecting the top surface of the wafer and detecting a defect of several hundred nanometers to several ten nanometers from a wafer portion located near the edge portion of the wafer to perform high-sensitivity inspection.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. An apparatus for inspecting defects, comprising:
an edge grip which grips an edge of a specimen;
an illuminating optical unit having a light source which emits light to illuminate the specimen from an oblique direction;
a detection optical unit having plural detectors installed in plural directions with respect to the specimen griped by the edge grip and which detect light from the specimen illuminated by the illuminating optical unit; and
a signal processor which receives outputs from the plural detectors receiving light from the specimen, respectively, and processes the received outputs to detect defects on the specimen;
wherein a surface and an edge of the edge grip are ground so that an intensity of light scattered from the edge grip is lower than an intensity of light diffracted from the edge grip.

2. The apparatus according to claim 1, wherein said plural detectors of said detection optical unit are installed at positions where diffracted light from the edge grip is not incident.

3. The apparatus according to claim 1, wherein at least one of the plural detectors of said detection optical unit installs a shutter to block the light diffracted from the specimen.

4. The apparatus according to claim 1, wherein said illuminating optical unit installs a polarizer to illuminate the specimen with a polarized light, and at least one of the detectors of the detecting optical unit installs a polarized filter to cut off diffracted light from the edge grip.

5. A method for inspecting defects, comprising the steps of:
gripping an edge of a specimen with an edge grip;
illuminating the specimen gripped by the edge grip from an oblique direction;
detecting light from the specimen, which is illuminated by the illuminating, with plural detectors installed in plural directions with respect to the specimen griped by the edge grip; and
receiving outputs from the plural detectors receiving light from the specimen, respectively, and processing the received outputs to detect defects on the specimen;
wherein in the step of detecting, at least one of the plural detectors detects light from the edge grip, which is ground, so that the light from the specimen and the light detected by the at least one of the plural detectors includes a scattered light scattered from the edge grip and a diffracted light diffracted from the edge grip, and an intensity of the scattered light is lower than an intensity of the diffracted light.

6. The method according to claim 5, wherein in the step of detecting, the light diffracted from the specimen is blocked by a shutter installed on a light path from the specimen to the at least one of the plural detectors.

7. The method according to claim 5, wherein in the step of illuminating, the specimen is illuminated by a polarized light, and in the step of detecting, at least one of the plural detectors detects light filtered by a polarized filter to cut off diffracted light from the edge grip.

* * * * *